United States Patent [19]

Baulcombe et al.

[11] Patent Number: 5,175,102
[45] Date of Patent: Dec. 29, 1992

[54] MODIFICATION OF PLANT VIRUSES OR THEIR EFFECTS

[75] Inventors: David C. Baulcombe, Cambridge, United Kingdom; Bryan D. Harrison, Inchture, Scotland; Michael W. Bevan, Cambridge, United Kingdom; Michael A. Mayo, Monifletch, Scotland

[73] Assignee: Agricultural Genetics Company, Limited, Cambridge, United Kingdom

[21] Appl. No.: 449,338

[22] Filed: Dec. 13, 1989

Related U.S. Application Data

[63] Continuation of Ser. No. 6,122, Jan. 23, 1987, abandoned.

[30] Foreign Application Priority Data

Jan. 23, 1986 [GB] United Kingdom ............... 8601680

[51] Int. Cl.⁵ .................... C12N 15/00; C12N 7/00; A01H 1/04
[52] U.S. Cl. .................... 435/172.3; 435/235.1; 435/320.1; 800/205; 935/30; 935/64; 935/67
[58] Field of Search ............... 435/172.3, 235.1, 320.1; 800/205; 935/30, 64, 67

[56] References Cited

U.S. PATENT DOCUMENTS 4,407,956 10/1983 Howell ........................... 435/172.3

FOREIGN PATENT DOCUMENTS 0223452 5/1987 European Pat. Off. .
0067553 12/1982 United Kingdom .

OTHER PUBLICATIONS

Kaper (1983) Plant Molecular Biology, Alan R. Liss, Inc., NY, pp. 81–100.
Sequeira (1984) Trends in Biotechnology 2(2):25–29.
Fraley et al (1983) Proc Nat Acad Sci. USA 80:4803–4807.
Beachy et al (1985) Biotechnoloby in Plant Science, Program and Abstracts, p. 13.

Ohgawara et al. 1983, Protoplasma 116:145–148.
Kaper et al., "Viral satellites: parasitic nucleic acids capable of modulating disease expression", *Endeavor*, vol. 8, No. 4 1984, pp. 194–200.
Dreher et al., "Mutant viral RNAs synthesized in vitro show altered aminoacylation and replicase template activities", Nature, vol. 311, 1984, pp. 171–174.
Bevan et al., "Expression of tobacco moisaic virus coat protein by a cauliflower mosaic virus promotor in plants transformed by *Agrobacterium*, EMBO Journal", vol. 4, No. 8, pp. 1921–1926, 1985.
Waterworth et al., "CARNA 5, the Small Cucumber Mosaic Virus–Dependent Replicating RNA, Regulates Disease Expression", *Science*, vol. 204, May, 1979, pp. 845–847.
Gerlach, et al., "Construction of a plant disease resistance gene from the satellite RNA of tobacco ringspot virus", *Letters to Nature* vol. 328, Aug. 1987, pp. 802–805.
Murant et al., "Satellites of Plant Viruses", *Ann. Rev. Phytopathol*, 1982, 20:49–70.
Loesch-Fries, et al., "Expression of alfalfa mosaic virus RNA 4 in transgenic plants confers virus resistance", *EMBO Journal*, vol. 6 No. 7, pp. 1845–±851, 1987.
Abel et al., "Delay of Disease Development in Transgenic Plants That Express the Tobacco Mosaic Virus Coat Protein Gene" *Science*, vol. 232, 1986, pp. 738–743.

(List continued on next page.)

Primary Examiner—David T. Fox
Attorney, Agent, or Firm—Lowe, Price, LeBlanc & Becker

[57] ABSTRACT

The invention relates to a method of modifying a plant virus or its effects, which comprises incorporating genetic material into a plant and infecting said plant with a plant virus, whereby expression of the incorporated genetic material modifies the plant virus or its effects. In a preferred embodiment, expression in the plant of the incorporated genetic material causes attenuation of the symptoms of attack on the plant by a plant virus.

14 Claims, 8 Drawing Sheets

```
*TY CMVSAT.LIS
GTTTGTTTG ATGGAGAATT GCGCAGAGGG GTTATATCTG CGTGAGGATC TGTCACTCGG
    10        20        30        40        50        60

CGGTGTGGGA TACCTCCCTG CTAAGGCGGG TTGAGTGATG TTCCCTCGGA CTGGGGACCG
    70        80        90        100       110       120

CTGGCTTGCG AGCTATGTCC GCTACTCTCA GTACTACACT CTCATTTGAG CCCCCGCTCA
    130       140       150       160       170       180

GTTTGCTAGC AGAACCCGGC ACATGGTTCG CCGATACCAT GGAATTTCGA AAGAAACACT
    190       200       210       220       230       240

CTGTTAGGTG GTATGAGTCA TGACGCACGC AGGGAGAGGC TAAGGCTTAT GCTATGCTGA
    250       260       270       280       290       300

TCTCCGTGAA TGTCTATCAT TCCTACACAG GACCC
    310       320       330          5         15        25

DIR CMV*
```

OTHER PUBLICATIONS

Jacquemond, et al., "A Gene Coding for a Monomeric Form of Cucumber Mosaic Virus Sateillite RNA Confers Tolerance to CMV", *Molecular Plant-Microbe Interactions,* vol. 1, No. 8, pp. 311-316, 1988.

Tien et al., "Satellite RNA for the control of plant diseases caused by cucumber moisaic virus", *Ann appl. Biol.,* (1987), III, 143-152.

Ponz et al., "Cherry Leafroll Virus Infections are Affected by a Satellite RNA that the Virus Does not Support", *Virology,* 160, 183-190 (1987).

```
*TY CMVSAT.LIS
GTTTGTTTG ATGGAGAATT GCGCAGAGGG GTTATATCTG CGTGAGGATC TGTCACTCGG
         10         20         30         40         50         60

CGGTGTGGGA TACCTCCCTG CTAAGGGGGG TTGAGTGATG TTCCCTCGGA CTGGGGACCG
         70         80         90        100        110        120

CTGGCTTGCG AGCTATGTCC GCTACTCTCA GTACTACACT CTCATTGAG CCCCGCTCA
        130        140        150        160        170        180

GTTGCTAGC AGAACCCGGC ACATGGTTCG CCGATACCAT GGAATTCGA AAGAAACACT
        190        200        210        220        230        240

CTGTTAGGTG GTATGAGTCA TGACGCACGC AGGGAGAGGC TAAGGCTTAT GCTATGCTGA
        250        260        270        280        290        300

TCTCCGTGAA TGTCTATCAT TCCTACACAG GACCC
        310        320        330        5          15        25

DIR CMV*

MODIFICATION OF PLANT VIRUSES OR THEIR EFFECTS

This application is a continuation of application Ser. No. 07/006,122 filed Jan. 23, 1987, now abandoned.

This invention relates to the modification of plant viruses or their effects.

The particles of some cultures of cucumber mosaic virus (CMV) contain, in addition to the three genomic species of single-stranded RNA and a sub-genomic species that acts as mRNA for CMV particle protein, another single-stranded linear RNA molecule that typically is about 335 nucleotides long. This extra molecule, known as satellite RNA, does not share any appreciable nucleotide sequence with CMV genomic RNA but replicates only in plants or protoplasts that are infected with CMV. CMV isolates that do not contain satellite RNA can be cultured repeatedly in plants in a satellite-free state, but when satellite RNA is added to such cultures it is synthesized and persists as a component of the virus isolate. The effect of satellite RNA on CMV infections varies between strains. In many cases the normal symptoms of CMV are suppressed and as a result the infected plants show no obvious signs of infection. However, the presence of other strains of satellite RNA leads to the production of severe symptoms which are quite distinct from those of CMV.

Since plants containing infections of CMV with some strains of satellite RNA show milder symptoms than infections without satellite, it has been proposed to use complete viruses containing satellite RNA to protect plants against the effects of CMV infections. Experiments have in fact shown that pre-infection with a CMV strain containing satellite RNA causes protection against CMV symptoms and leads to increased yield of pepper plants. It has also been shown that infection of tomato plants with CMV strains containing a benign satellite RNA results in a cross protection against the effects of CMV strains with a virulent satellite RNA. However, the use of a complete virus as the prophylactic agent may cause several problems. The protecting strain may itself have adverse effects on growth and yield or may be a reservoir for infection of other plant species. It is also possible that the avirulent strain may mutate to virulence.

We have sought to eliminate these difficulties by the strategy demonstrated in this invention in which biologically active, preferably virus-derived genetic material, in particular satellite RNA, is maintained in the plant by transcription from the nuclear genome.

The present invention provides a method of modifying a plant virus or its effects, which comprises incorporating genetic material into a plant and infecting said plant with a plant virus, whereby expression of the incorporated genetic material modifies the plant virus or its effects.

The genetic material to be incorporated is preferably derived, optionally with modification, from a plant virus which is the same as or different from the plant virus which is to infect the plant.

In a preferred embodiment, expression in the plant of the incorporated genetic material causes attenuation of the symptoms of attack on the plant by a plant virus.

The genetic material transferred into the plant is preferably cDNA corresponding to plant viral satellite RNA, the cDNA and/or the satellite RNA optionally having been modified.

Expression of viral RNA may protect the plant against the pathogenic effects of a related viral RNA. Alternatively, expression of RNA of viral origin may protect against the pathogenic effects of a viral RNA which does not have sequence homology. It should also be noted that the expression of viral genetic material, as RNA, may exert its effect independently of the translation of that RNA into protein.

The invention also provides a method of genetically engineering a plant, which comprises incorporating into the nuclear genome of the plant DNA which is capable of being expressed in the plant and capable upon challenge of the plant by a plant virus, of modifying said plant virus or its effects. The invention further relates to a plant which has been genetically engineered by such a method, as well as the progeny of such a plant.

Viruses which are particularly suitable for use in the invention are those having relatively low molecular weight satellite RNA, generally with less than 1000 nucleotides. Examples are Cucumber Mosaic Virus, or other cucumoviruses, Tobacco Ringspot Virus, or other nepoviruses, Tomato Bushy Stunt Virus or other tombusviruses, Turnip Rosette Virus and sobemoviruses or other viruses allied to them. Any plants which can be infected by such viruses can be used in the invention.

Preferably the virus is cucumber mosaic virus (CMV) and the genetic material used for transformation is cDNA corresponding to CMV satellite RNA. The cDNA is preferably transferred into an expression vector which allows transfer of DNA into the nuclear genome of a recipient plant, for example an expression vector based on the Ti plasmid system of *Agrobacterium tumefaciens*.

The invention thus also provides an expression vector capable of transferring DNA into the nuclear genome of a recipient plant, characterised in that it incorporates transferable DNA capable of being expressed in the recipient plant and capable, upon challenge of the plant by a plant virus, of modifying said plant virus or its effects. The expression vector is preferably a plasmid including the T-DNA border sequences from a Ti plasmid of *Agrobacterium tumefaciens*, a transcriptional promoter, cDNA corresponding to CMV satellite RNA, and a transcriptional terminator.

Cells of the plant to be protected, e.g. leaf disks, are infected by a strain of *A. tumefaciens* harbouring the expression vector and whole plants are regenerated from infected cells which have been transformed.

It has been shown in several laboratories that the Ti plasmid of Agrobacterium can be used to introduce novel DNA sequences into the nuclear DNA of plants. It has further been shown that if these DNA sequences contain appropriate promoter and terminator sequences, then the DNA is transcribed into RNA in the transformed cells. Any other methods and vectors for the introduction of novel DNA sequences and which are not related to Agrobacterium are also suitable for use in this invention, provided that a transcriptional promoter and transcriptional terminator are incorporated into the vector molecule as an expression cassette for the appropriate viral sequence. The use of direct DNA uptake methods for the transformation of plant cells is also possible and has been shown in the following articles:

Krens, F. et al. Nature 296, 72–74 (1982)
Paskowski, J. et al. EMBO J. 3, 2717–2722 (1984)
Hains, R. et al. Mol. Gen. Genet. 199, 161–168 (1985)
Potrykus et al. ibid. 199, 183–188 (1985)

Fromm et al. Nature, 319, 791-793 (1986)

We have demonstrated that satellite RNA multimers are processed into unit length molecules and subsequently replicated if co-infected into tobacco plants with CMV-RNA. This observation was important because the methods of achieving expression of novel DNA as RNA in transformed cells require that the RNA transcripts include sequence from the transcriptional terminator and promoter regions. Work on other viral systems had suggested that addition of foreign sequence to the termini of viral RNA molecules affected the ability of that RNA to replicate. In the absence of proof that the satellite RNA could be generated by processing from a multimer, it seemed that the most likely outcome of an experiment in which a cDNA copy of satellite RNA was expressed as RNA in transformed cells was that the transcript would not be replicated by the incoming virus. Since the action of satellite RNA in inhibition of viral symptoms is likely to be mediated by competition between satellite and viral RNA for replication machinery, this would imply that the satellite transcript in the transformed cells would not affect CMV symptom production.

However, having established that satellite RNA could be processed from multimers it became evident that biologically active satellite RNA could be expressed in transformed plant cells. The primary transcription product would be multimeric satellite RNA molecules containing additional sequence at the termini from the promoter and from the transcriptional terminator. It was predicted that, either before or following CMV infection, the satellite multimer transcript would be processed into unit length molecules which would then undergo normal satellite RNA activity in CMV infected cells. This activity would, it was predicted, include replication and symptom attenuation. This description outlines the construction of cDNA clones containing satellite RNA as multimeric structures and the insertion of these sequences into a Ti plasmid expression vector. The biological activity of multimer transcripts of satellite RNA has been demonstrated in cells of transformed tobacco.

Reference is now made to the accompanying drawings, in which.

EXAMPLES

In order to illustrate an embodiment of the invention we describe the transformation of tobacco plants with DNA copies of CMV satellite RNA, the production of satellite RNA transcripts by such plants and the acquisition of satellite RNA by CMV cultures grown in them.

The satellite RNA used in this work was isolated from CMV strain $I_{17}N$ (ref 20) and was cloned as complementary DNA (cDNA). The nucleotide sequence of the cDNA clone was very similar to that of other strains of CMV. Two head-to-tail concatemeric satellite cDNA molecules were constructed. These comprised one (pT104) or two (pT105) complete satellite RNA sequence units with incomplete units at the 5' end (FIG. 3) and were intended to mimic multimeric satellite RNAs which are thought to be replication intermediates. To achieve expression of these satellite sequences in transformed plants, the cDNA molecules were transferred into an expression vector (Rokl) based on the binary Ti plasmid system of *Agrobacterium tumefaciens*. The resultant plasmids are referred to as Rokl/104 and Rokl/105.

The description is in four parts: isolation and purification of satellite RNA; cloning of satellite RNA as cDNA; construction of satellite cDNA multimers; transfer of satellite cDNA into a Ti plasmid.

ISOLATION AND PURIFICATION OF SATELLITE RNA

Plants of *Nicotiana clevelandii* were infected with cucumber mosaic virus (strain $I_{17}N$, provided by Dr. M. Jacquemond, INRA, Montfavet, France) and the virus particles isolated and purified exactly as described by Lot et al. (ref 1). RNA was extracted from virus particles by the addition of sodium dodecyl sulphate to 1%, extraction with buffer saturated phenol (50 mM Tris-HCl pH8) and ethanol precipitation. The RNA was recovered by centrifugation and was resuspended at 0.5 mg ml$^{-1}$ in water. Satellite RNA was purified by sucrose gradient centrifugation. 33 μg of CMV RNA was diluted to 100 μl of $H_2O$ and 2 μl of 1M Tris-Borate buffer (pH8) was added with 5 μl of 1M methyl mercuric hydroxide. After 5 min at room temperature 5 μl of β-mercaptoethanol was added and the sample was loaded onto a 5-20% (w/v) sucrose gradient in tubes of a Sorvall AH650 rotor. The gradient was buffered with 10 mM Tris-HCl pH 7.5, 100 mM NaCl, 1 mM ethylene diamine tetraacetic acid (EDTA) pH8. The gradient was centrifuged for 2 h at 50000 rpm at 20° C. and 20 equal volume fractions were collected by dripping from the bottom. Aliquots (20 μl) from each fraction were assayed by electrophoresis in an agarose gel which was stained with ethidium bromide to detect the presence of satellite RNA. The fractions which contained satellite RNA were combined and the satellite RNA was collected by ethanol precipitation and dissolved in 20 μl of distilled water.

CLONING OF SATELLITE RNA AS COMPLEMENTARY DNA (cDNA)

To facilitate priming of cDNA synthesis, a polyadenylate sequence was added to the 3' end of the satellite RNA. 10 μl of the satellite RNA was incubated in 25 μl of 25 mM Tris-HCl pH 7.9 250 mM NaCl with 2.5 mM $MnCl_2$, 500 μM ATP, 15U of placental ribonuclease inhibitor and 0.2U of poly A polymerase for 15 min at 37° C. The reaction was terminated by dilution to 75 μl and extraction with phenol. The polyadenylated satellite was then precipitated twice with ethanol and resuspended in 10 μl of distilled water.

The synthesis of cDNA from this RNA was primed with oligo $dT_{12-18}$ in a reaction volume of 25 μl which contained 25 mM Tris-HCl pH 8.3, 10 mM KCl, 4 mM $MgCl_2$, 0.025 mg ml$^{-1}$ oligo $dT_{12-18}$, 5 mM dithiothreitol, 500 μM each of dATP, dGTP, dCTP and TTP, 15U of placental ribonuclease inhibitor, 15U of reverse transcriptase and 10 μCi of $^{32}P$ (αlabelled)

dATP (≃500 Ci mmol) (New England Nuclear). After 1 h at 42° C. the reaction was boiled for 1 min, cooled in ice for 10 min and centrifuged at 10000×g for 10 min. The supernatant was added to 2.5 μl of 1M HEPES buffer pH7, 0.5 μl each of 20 mM dATP, dGTP, dCTP and TTP, 1.5 μl of 0.1M KCl, 2.6 μl of water and 5U of DNA polymerase I (Klenow fragment). The DNA was then passed through a 1 ml column of Sephadex G-50, ethanol precipitated and resuspended in 50 μl of 0.3M NaCl, 0.03M NaOAc (pH 4.5), 4.5 mMZnSO$_4$, 5% glycerol containing 3000U ml$^{-1}$ of S1 nuclease. After 1 h at 37° C. the reaction was diluted by the addition of 50 μl TE and the sample layered over a 5-20% sucrose gradient in 10 mM Tris-HCl pH 7.5, 1 mM EDTA, 100 mM NaCl and centrifuged for 4 h at 50000 rpm in a SORVALL AH 650 rotor. The gradient was fractionated from the bottom and the largest 50% of cDNA molecules, detected by monitoring radioactivity in fractions, were pooled into one fraction. The sample was extracted with phenol/chloroform, precipitated with ethanol and collected by centrifugation at 40000 rpm for 30 min in a SORVALL AH 650 rotor. The samples were reprecipitated with ethanol from 100 μl, rinsed with ethanol and dried and dissolved in 10 μl of 1 mM Tris-HCl pH8, 0.1 mM EDTA.

The cDNA was then incubated with terminal transferase and dCTP, to add oligo dC tails which would facilitate cloning of the cDNA into the plasmid vector. The reactions contained 5 μl of cDNA, 1 μl of 10×buffer (1.4M cacodylic acid, 0.3M Tris base, 1.1M KOH), 0.2 μl of 10 mM dCTP, 0.1 μl of 20 μM dithiothreitol, 1.7 μl of water, 1 μl of 10 mM CoCl$_2$ and 10U of terminal transferase. The reaction was incubated for 10 minutes at 37° C. and then stopped by incubation at 65° C. for 2 minutes.

The vector for cloning was the plasmid pUC9 (ref 2) which was digested with PstI and tailed with dGTP in a similar reaction with terminal transferase. The tailed cDNA (4 μl) was annealed with tailed plasmid (80 ng) in 30 μg of 10 mM Tris-HCl pH 7.4, 100 mM NaCl, 0.1 mM EDTA. The reaction was heated to 65° C. and cooled to 4° C. overnight. Aliquots (5 μl) of the annealing mix were transformed into *E. coli* strain MC1022 and plated onto ampicillin with indicators (1PTG and Xgal) for the presence of a cDNA insert in the LacZ gene. Colonies showing no blue colour were selected for further analysis.

Initially the plasmid DNA was analysed for the presence of an insert which hybridised to purified satellite RNA. Subsequently, having confirmed this, plasmid DNA was purified and the size of the insert was determined by digestion with PstI and electrophoresis in polyacrylamide.

For one of the clones, designated B7, the insert size was shown to be approximately 410 bp. This indicated that the cDNA insertion would contain most or all of the satellite sequence (335 bp), combined with the homopolymer tails added as described above to facilitate cloning.

Figure 1:
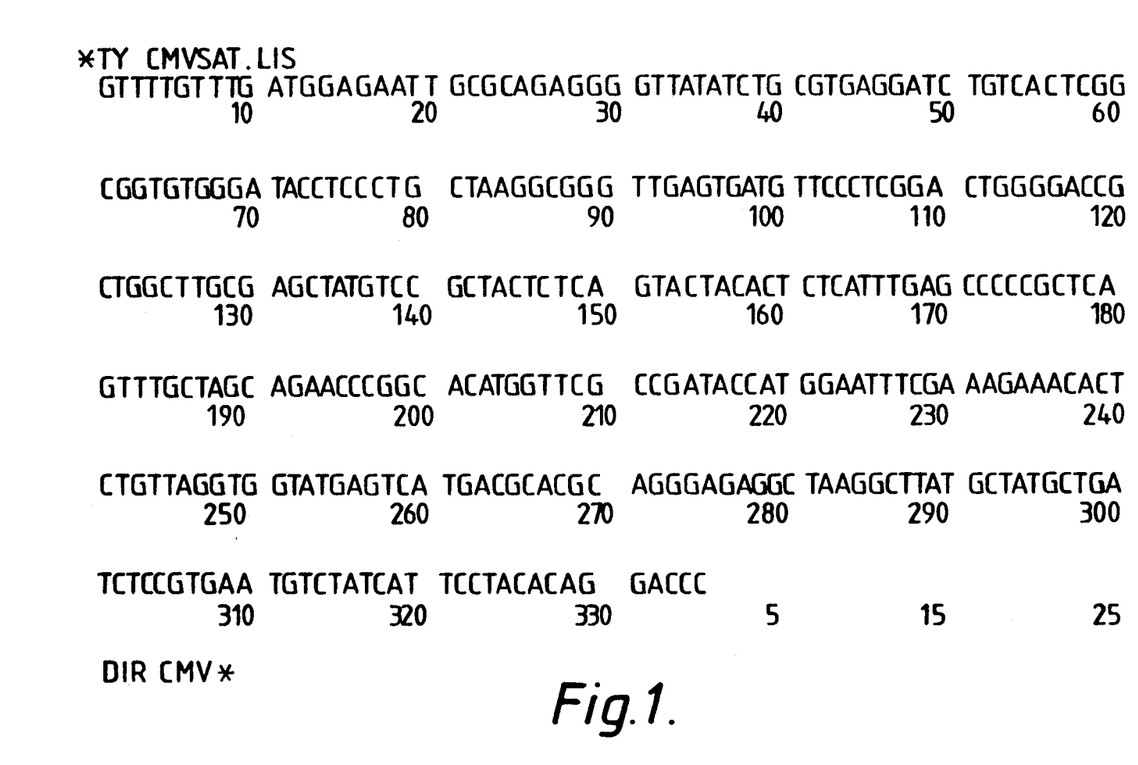
FIG. 1 shows the nucleotide sequence of cDNA corresponding to CMV satellite RNA.

To confirm the extent of the cDNA in the insert of B7, the nucleotide sequence was determined using the method of Maxam and Gilbert (ref 3) and is shown in FIG. 1. The sequence was very similar to that of other CMV satellite RNA molecules determined directly from the RNA, exept that 3 nucleotides at the 5' end were absent from the cDNA, presumably as a result of incomplete copying by reverse transcriptase.

The subsequent manipulations could be carried out with clones showing different degrees of completeness at the 5' end, except that different oligonucleotide reagents (see page 13) would be used to compensate.

CONSTRUCTION OF SATELLITE cDNA MULTIMERS

For the reasons described in the introductory section, it was considered necessary to construct multimeric copies of the satellite cDNA. These were a complex series of manipulations outlined in FIG. 2 in which the aims were to, firstly remove the homopolymer tails from the 3' of the satellite sequence. The cDNA molecules were then constructed with a dimeric structure, which included at the junction between the two satellite sequences, the 5' homopolymer tail. The next step was to clone out the junction region and, using oligonucleotide directed mutagenesis techniques to remove the 5' homopolymer tail, and to replace the missing 3 nucleotides from the 5' end. The modified junction region was then joined to a restriction fragment containing the satellite cDNA to create structures which contained one or two complete units of satellite sequence. These manipulations are described in more detail below.

a) Removal of Homopolymer Tails from the 3' of the Satellite Sequence

Figure 2:
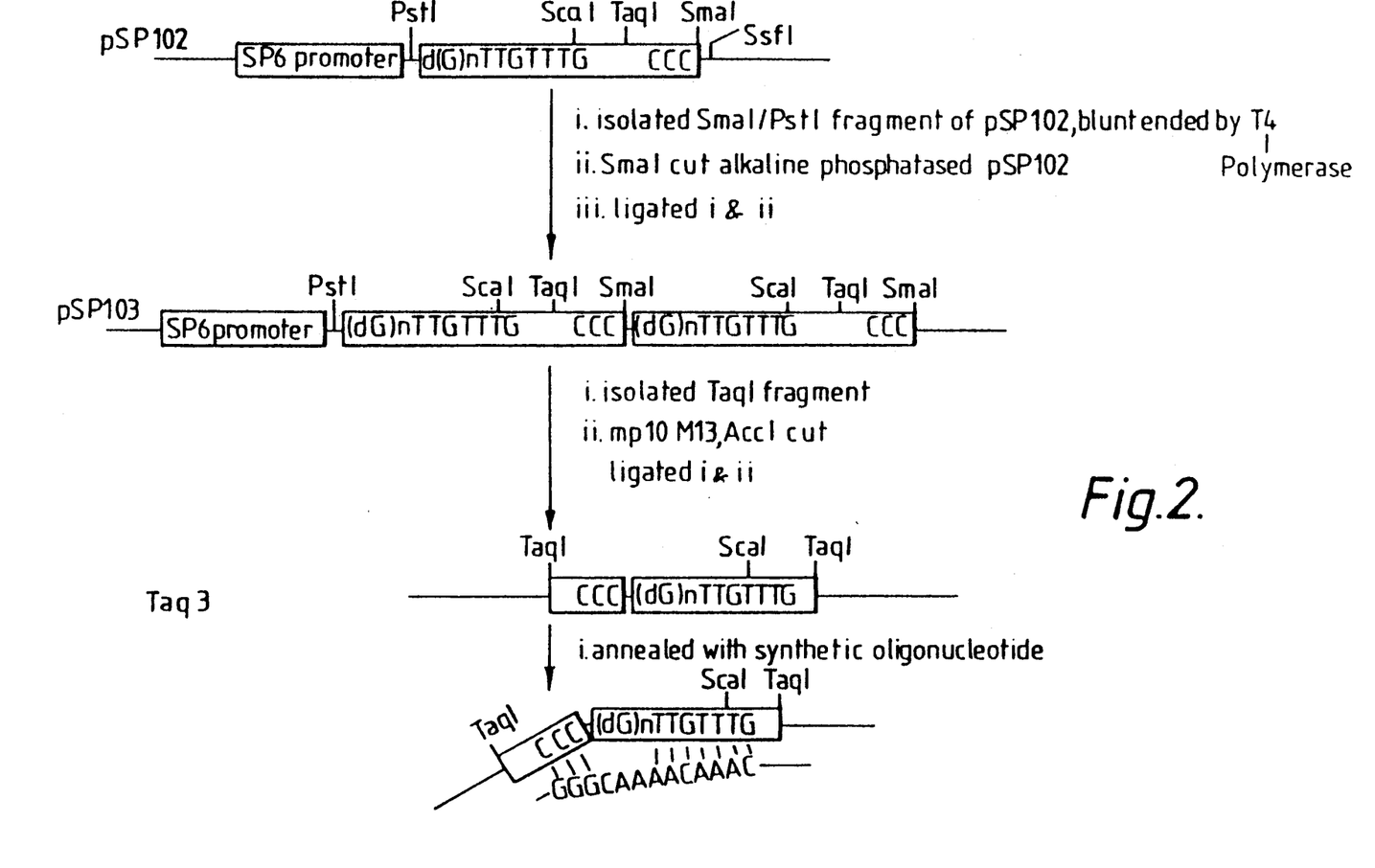
FIG. 2 is an outline scheme for the construction of satellite cDNA multimers.

This was achieved using Bal 31 nuclease. First 60 μg of the plasmid B7 was rendered linear by cutting with BamHI. B7 contains a single BamHI site which is located adjacent to the PstI site where the cDNA was inserted, and on the 3' side of the insertion. The DNA was then phenol extracted, ethanol precipitated and suspended in 400 μl of 10 mM Tris-HCl (pH 8) 1 mM EDTA. 100 μl of Bal 31 buffer was added and 0.5U of Bal 31 nuclease. 130 μl aliquots were removed at 8, 12, 16 minutes and extracted with phenol. The DNA was then collected by ethanol precipitation. The ends of the Bal 31 digested DNA were treated with T4 DNA polymerase in order to remove overhanging 3' ends and to fill in recessed 3' ends. The reaction contained TA buffer (33 mM Tris-acetate pH 7.9, 66 mM K acetate, 10 mM Mg acetate, 4 mM spermine, 0.5 mM dithiothreitol), 2.5 μM of dATP, dGTP, dCTP and TTP and 5U of T4 DNA polymerase in 45 μl. After 3 h at 37° C. the reaction was diluted to 100 μl and the DNA digested with PstI to release two fragments. The larger one was the vector plasmid deleted from the BamHI site. The smaller was the cDNA inserts extending from the 5' PstI site to the site of the Bal 31 deletion. In order to isolate the deleted cDNA molecules extending approximately to the terminal nucleotides of the cDNA insert (... CCC$_{OH}$) and not into the homopolymer tails, the DNA was fractionated on a 5% polyacrylamide gel and the cDNA fragments of approximately 350 nucleotides were isolated. These fragments were then cloned into pUC9 which had been digested with PstI and SmaI. Since the terminal nucleotides of the cDNA represent the 5' nucleotides of a SmaI site, the clones containing a deletion to the precise 3' end of the cDNA could be recognised by the presence of a SmaI site in the recombinant plasmid. One clone, designated D26 was identified which met this criterion. The presence of the correct insert was confirmed by digestion with other restriction enzymes. The insert of this clone was transferred to another plasmid, pSP6/4 (ref 4) for the purposes of another experiment although this was not essential for the manipulations described here. Subsequent manipulations were based on the construction of D26 in pSP6/4, which was designated pSP102. The relevant features of pSP102 are shown in FIG. 2.

b) Mutation of Junction Region

The next step involved the addition of a second satellite cDNA insertion into pSP102 to create a head to tail dimer structure. To do this, the insert of pSP102 was released by digestion of 10 μg DNA with SmaI and PstI. The protruding 3' end of the PstI site was rendered blunt by the addition of dATP, dGTP, dCTP and TTP to 100 μM and 4U of T4 polymerase in 25 μl. Following incubation at 37° C. for 15 minutes the cDNA insert was purified by fractionation on a 5% polyacrylamide gel. This cDNA insertion was then cloned into the SmaI site of pSP102 and the resultant clones were screened for the presence of an insertion in the head to head, or head to tail configuration by digestion with TaqI. One clone with the head to tail dimer was designated pSP103.

In order to mutate the junction region of the dimer so that the homopolymer tail was removed, and so that the 5' nucleotides thought to be missing from the cDNA were restored, it was necessary to clone the junction region clones into a single stranded phage vector, mp10 (ref 5). It was also necessary to obtain a synthetic oligonucleotide which represent the complement of the sequence in the corrected junction. This oligonucleotide was purchased from Dr. S. Minter (UMIST) and was the sequence TCCATCAAACAAAACGGGTCCTGTGTAGGA (within this the sequence GGG is the complement of the 3' end of the satellite RNA and the sequence AAAAC the complement of the 5' end of the satellite, including the missing nucleotides).

The DNA of pSP103 extending between the TaqI sites, shown in FIG. 2 was cloned into mp10, at the AccI site. Single stranded DNA from this clone, which was designated Taq3, was isolated by standard procedures (ref 5).

The synthetic oligonucleotide was prepared for use by reaction with ATP and polynucleotide kinase. The reaction contained 15 pmol of oligonucleotide, 70 mM Tris.HCl pH 7.6, 10 mM $MgCl_2$, 5 mM dithiothreitol, 1 mM ATP and 10U of polynucleotide kinase in 20 μl. The reaction was incubated at 37° C. for 1 h and stopped by heating at 70° C. for 10 min.

The kinase oligonucleotide (5 pmol) was then annealed to 2 μg of DNA from Taq3 with 25 ng of sequence primer (a synthetic oligonucleotide with the sequence GTAAAACGACGGCCAGT, obtained from New England Biolabs) with 10 mM Tris-HCl pH8, 1 mM EDTA in a reaction volume of 12 μl. The reaction was initiated at 80° C. in a 250 ml beaker of water which was then cooled to 15° C. on ice. To this was then added the following: 1 μl of 100 mM Tris-HCl pH8, 10 mM $MgCl_2$, 1 μl of 5 mM dATP, dGTP, dCTP and TTP, 1 μl of 5 mM ATP, 1 μl 0.1M dithiothreitol, 4 μl of water, 1U of DNA polymerase I (Klenow fragment) and 6U of T4 DNA ligase. The reaction was incubated for 4 h at 15° C. and diluted with 180 μl of 10 mM Tris-HCl ph8, 1 mM EDTA. 1 μl aliquots of this were transformed into E. coli (strain JM101).

The resultant plaques were hybridised with the synthetic (junction sequence) oligonucleotide, labelled with $^{32}P$ in order to detect clones containing the mutated (corrected) junction region. The mutated clones were distinguished from non-mutated clones by increased stability of the resultant hybrids.

To label the synthetic oligonucleotide, the reaction contained 15p mol of oligonucleotide, 200 μCi of $^{32}P$ labelled (γposition) ATP (3000 Ci mmol), 70 mM Tris-HCl pH 7.6, 10 mM $MgCl_2$, 5 mM dithiothreitol and 10U of polynucleotide kinase. The reaction was incubated at 37° C. for 30 min and heated at 70° C. to stop the reaction. For the hybridisation step, a replica of the phage plaques was formed on a nitrocellulose filter by layering the filter on the plaques for 30 sec. The filter (9 cm diameter) was then floated on 0.5N NaOH, 0.5M NaCl for 1 min and twice for 1 min on 1.5M NaCl, 0.5M Tris HCl pH 7.5. The filter was then baked in vacuo at 80° C. for 2 h, prehybridised in 1M NaCl, 33 mM PIPES pH 6.8, 6.6 mM EDTA, 0.2% gelatin, 0.2% Ficoll, 0.2% polyvinylpyrollidone 360, 0.1% sodium dodecyl sulphate for 1 h at 65° C. and then hybridised with the $^{32}P$ oligonucleotide (1.5 pmol) in 1 ml of 1M NaCl, 33 mM PIPES pH 6.8, 6.6 mM EDTA for 16 h at 25° C. The filter was then rinsed several times in 0.9M NaCl, 0.09M sodium citrate and autoradiographed to detect the hybridisation. The filter was then washed at 42° C., 52° C., 62° C. and 72° C. in 0.9M NaCl, 0.09M sodium citrate and the hybridisation was monitored by autoradiography in between each temperature step.

Of the plaques showing stable hybridisation at 62° C. and 72° C., six were selected and cultured. Single stranded DNA was prepared by standard procedures (ref 5), and the sequence across the junction region was confirmed using the dideoxy sequencing method of (ref 6). These clones were designated Taq 3'.

To build up the multimeric satellite units containing this corrected junction region it was necessary to obtain sufficient quantities of the DNA in double stranded form. This was achieved by cloning the TaqI fragment containing the junction region from Taq 3' into a plasmid vector. The single stranded Taq 3' DNA (25 μl) was incubated in 75 μl with 40 ng of sequencing primer defined above and 10 μl of 100 mM Tris-HCl pH8, 10 mM Mg $Cl_2$ at 65° C. for 1 h. To this was added 20 μl of 5 mM dATP, dGTP, dCTP, TTP and 25U of DNA polymerase I (Klenow fragment). After incubation at 20° C. for 30 min the sample was digested with EcoRI and HindIII (50U each) and incubated at 37° C. for 1 h. These enzymes excised the Taq 3' DNA adjacent to either side of the junction fragment cDNA. The released junction fragment was subsequently purified by polyacrylamide gel electrophoresis and cloned into plasmid vector pUC9. One clone containing the desired fragment of Taq 3' was identified by restriction enzyme digestion and designated pUS1.

c) Construction of Satellite Multimers

To construct a cDNA containing the junction fragment of pUS1 joined to a cDNA fragment extending from the TaqI$^a$ site through to the 3' terminus of the satellite DNA, the following manipulations were carried out.

First the ScaI/SstI fragment of pSP102 and the BamHI/ScaI fragments of pUS1 were isolated by polyacrylamide gel electrophoresis and ligated together with vector DNA (pT7/2, ref 7) digested with BamHI and SstI. The choice of vector was determined by a different experiment. Other vectors (e.g. pUC9) could have been substituted for this. The clones containing the correct insertion of the two fragments from pUS1 and pSP102 were identified by restriction enzyme digestion with BamHI and SstI (producing the inserted cDNA of approximately 450 nucleotides). One of these was designated pT104.

Although the prediction, outlined in the introduction was that multimeric transcripts would be processed in transformed plants, it was not possible to predict from the information available the precise constructions which would be necessary to produce this result. For example, if the sequence determining the processing reaction is contained internally to the processed unit then expression of the pT104 construction would be adequate. If, however, the necessary sequence is located externally to the processed unit then it would be necessary to express a multimeric transcript which contained satellite cDNA sequence on both sides. For this reason a further construction was made containing two complete satellite units flanked on the 5' side by an incomplete unit.

In order to make this construction the pT104 and the pUS1 DNAs were digested with TaqI under conditions where plasmid molecules were excised, on average, once per molecule. The digested DNA was then fractionated on a 0.7% agarose gel and the full length linear molecules were isolated. The pT104 DNA was then digested with SstI and fractionated on a 5% polyacrylamide gel in order to isolate fragments of the size predicted (approximately 450 bp) for the distance between TaqI$^a$ site and the SstI site (FIG. 2). Similarly, pUS1 was digested with BamHI and fragments were isolated to the size predicted (approximately 350 bp) for the BamHI/TaqI$^b$ fragment (FIG. 2). These fragments were combined, ligated with pT7-2 digested with BamHI and SstI and transformed into *E. coli*. Several clones were identified containing the desired insertion and one of these was designated pT105.

TRANSFER OF SATELLITE cDNA MULTIMERS INTO A Ti PLASMID

To obtain expression of satellite sequences in transformed plants the cDNA insertions of pT104 and pT105 were transferred into an Agrobacterium Ti plasmid vector called Rok1, which was obtained from M. Bevan. This is based on the vector Bin 19, described previously (ref 8), containing additionally a promoter and transcriptional terminator, and a BamHI site between these for insertion of new sequence. The promoter and terminator were as described previously (ref 9) in a vector constructed for the expression of a viral coat protein in transformed cells, with the difference that the promoter of Rok1 contained 6 nucleotides on the 3' side of the transcriptional initiation point, whereas the promoter used previously contained 132 bp in this region.

The Rok1 DNA (5 μg) was digested with BamHI in 40 μl and then treated with T4 DNA polymerase 5 U and 100 μM each of dATP, dGTP, dCTP and TTP for 15 min at 37° C. and 10 min at 65° C. To this was then added 0.6 U of calf intestinal phosphatase and the DNA was incubated at 37° C. for 60'. Following treatment at 65° C. for 10 min the DNA was extracted with phenol and precipatated with ethanol. The pT104 and pT105 DNAs were digested with BamHI and EcoRI and treated in a volume of 50 μl with 2.5 U of DNA polymerase I (Klenow fragment) with 50 μM each of dATP, dGTP, dCTP and TTP for 15 min at 37° C. The DNA was then fractionated on a 5% polyacrylamide gel and the satellite cDNA insertions were isolated.

Figure 3:
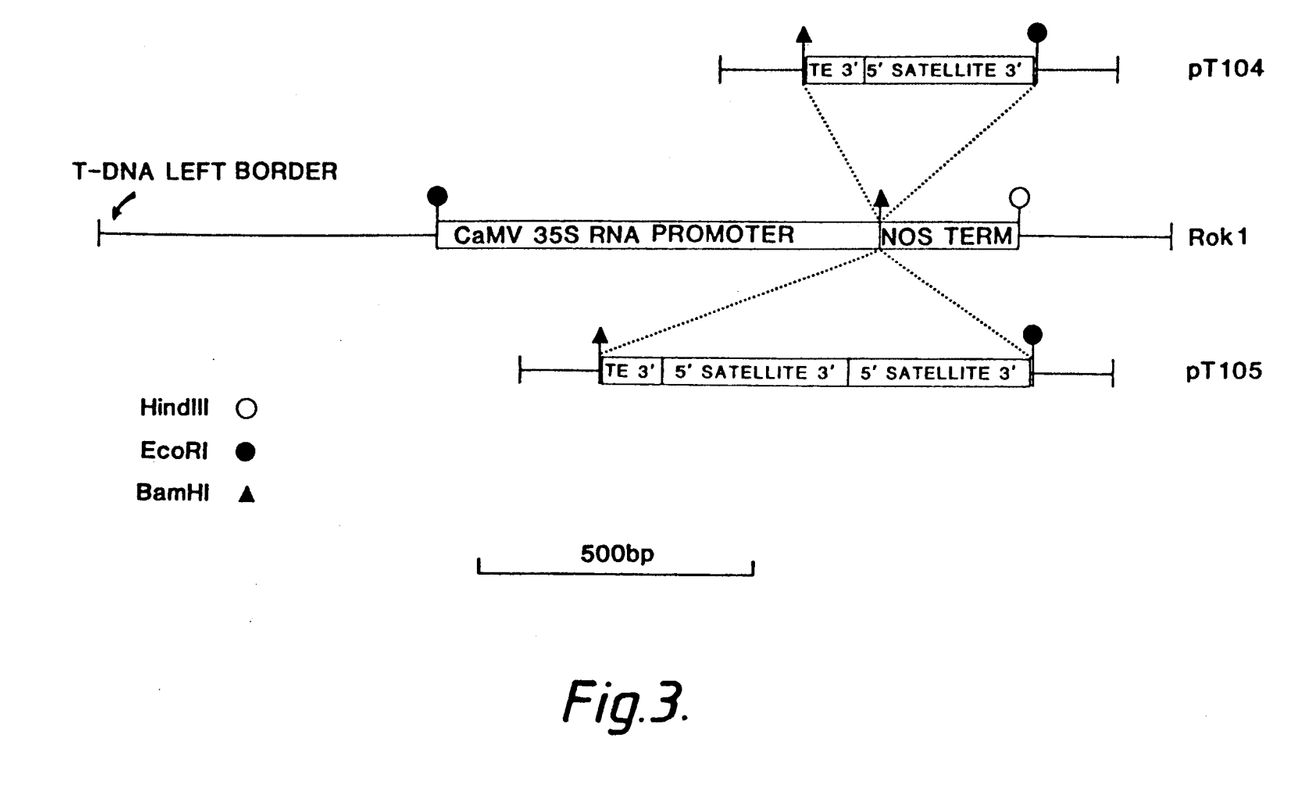
FIG. 3 is the detailed structure of the CMV satellite cDNA molecules in the binary Ti plasmid expression vectors.

FIG. 3 shows the detailed structure of the CMV satellite cDNA molecules in the binary Ti plasmid expression vectors. At the 5' of the 104 construction there are 51 nucleotides from the polylinker of plasmid pT7-2 extending from the transcriptional start point and including polylinker sequences of pT7-2 and other vectors used in the construction of pT104. On the 3' end of this as shown in the diagram there are 98 nucleotides extending from position 227 of the satellite sequence through to the 3' nucleotide of the satellite unit at position 335 ("TE 3'"). Immediately 3' of this there is a complete satellite unit, in the same orientation as the incomplete unit, flanked at the 3' end by 16 nucleotides extending between the SamI site and the EcoRI site of vector plasmid pT7-2 (ref 7). The 105 construction is as 104, except that two complete satellite units, in the same orientation, are present. The insertions from 104 and 105 were excised by digestion with restriction endonucleases BamHI and EcoRI, rendered blunt ended by the action of DNA polymerase (Klenow fragment) and inserted into the BamHI site of binary Ti plasmid Rok1. The BamHI site of Rok1 was rendered flush ended by the action of DNA polymerase (Klenow fragment). Rok1 is a derivative of the binary vector Bin19, described previously (ref 8), containing additionally an expression cassette inserted into the polylinker site. The expression cassette comprised the promotor of cauliflower mosaic virus 35S RNA (ref 10) and the terminator fragment of the nopaline synthase (nos) gene of Agrobacterium T-DNA (ref 11) (NOS TERM). It is essentially similar to the expression cassette described for the expression of tobacco mosaic virus coat protein gene (ref 9) except that the promoter fragment was deleted back to 6 bp 3' of the cap site of the 35S transcript using Bal31 nuclease. The unique BamHI site was inserted between the promoter and terminator fragments. Transcripts derived from this cassette would contain 10 nucleotides from the promoter and 200 nucleotides from the terminator (ref 11) in addition to the sequence inserted at the BamHI site.

The figure shows only the region adjacent to the cDNA insert of pT104 and pT105 and the expression cassette region of Rok1.

The digested Rok1 DNA was then ligated separately with the insertion of pT104 or p105 and transformed into *E. coli*. Recombinant clones were identified by digestion with EcoRI and HindIII (see FIG. 3 for location of these sites) and the plasmids containing the required insertions designated Rok1/104 or Rok1/105 respectively. These plasmids were then transferred into Agrobacterium by mating as described (ref 8). The resultant Agrobacterium strains were then used to transform cells in leaf discs of *Nicotiana tabacum* (var Samsun NN) using exactly the procedure of Horsch et al. (ref 12) except that (i) the leaves used were from axenically-grown plants, and were not sterilised; (ii) the selection of transformed plant cells was on 100 μg ml$^{-1}$ kanamycin.

Mature plants were regenerated from the transformed plants, also as described by Horsch et al. (ref 12).

The analysis of these plants is described below.

Transformed tobacco plants (cv. Samsun NN) were regenerated from Agrobacterium-infected leaf disks and were assayed for the presence of the satellite sequence in DNA and RNA by Southern and Northern blot analysis, respectively. The Southern blot analysis showed that the DNA of transformed plants contained the equivalent of 1-3 copies of the satellite cDNA per haploid genome. It was also shown, by Southern blot analysis, that the cDNA sequence, the promoter site and the RNA termination site had not been rearranged or deleted. The Northern blot analysis (FIG. 4) showed transcripts of about 700 nucleotides (Rok1/104) or 1000 nucleotides (Rok1/105), which are the approximate sizes predicted from the location of promoter and terminator sequences in the original constructions (FIG. 3) and allowing for the presence of a 3' polyadenylate tract. These RNA molecules were readily detected in total RNA or in polyadenylated RNA. No virus-like symptoms or other abnormalities in growth, flowering or seed production were observed in the transformed plants.

Figure 4:
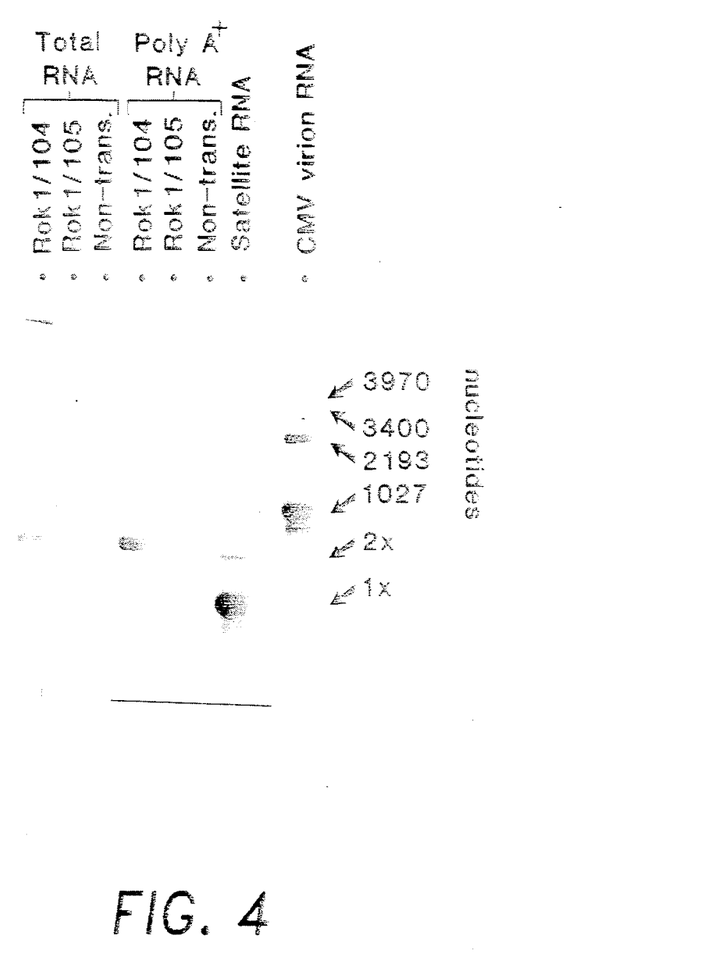
FIG. 4 is a Northern blot analysis of RNA from transformed plants.

FIG. 4 is a Northern blot analysis of RNA from transformed plants.

Total RNA (20 µg) or poly A+ RNA (1 µg) was isolated from leaves of non-transformed plants (non-trans) or plants transformed with Rok1/104 and Rok1/105 and fractionated on formaldehyde/agarose gels. The transcribed satellite RNA sequences were detected by blotting the gel onto nitrocellulose and hybridisation with nick translated insert from pT105. Total RNA from cells infected with CMV which contained satellite RNA was included as a reference for satellite RNA unit length (1×) and dimer length (2×) molecules. The size markers were virion RNA of CMV, which was detected with a cDNA clone (C20) of CMV genomic RNA (DCB, unpublished). This hybridised with CMV RNA-3, CMV RNA-4 and faintly with CMV RNA-1 and RNA-2. The size values given are those of Gould and Symons (ref 13). Methods. The constructions of 104 and 105 in Rok1 were mobilised into Agrobacterium strain LBA 4404 using *E. coli* strain HB101 harbouring pRK2013 in a triparental mating, as described (ref 8). The resultant Agrobacterium strains containing the binary vector constructions were then used to infect leaf disks from axenically grown *Nicotiana tabacum* (cv. Samsun NN). The infected and transformed cells were regenerated into plants by culturing the disks successively on a layer of tobacco feeder cells and then on shoot and root inducing medium as described by Horsch et al. (ref 12). The shoot and root induction media contained kanamycin at 100 µg ml$^{-1}$ to select for cells expressing the neomycin phosphotransferase gene contained in the T-DNA region of Rok1 (from Bin19) (ref 8). Transformed plants were propogated by transfer of stem cuttings into root induction medium.

RNA isolations were as described by Apel and Kloppstech[27] (ref 14) and electrophoresis and blotting analysis as described by Goldberg (ref 15) and Thomas (ref 16).

Figure 5A:
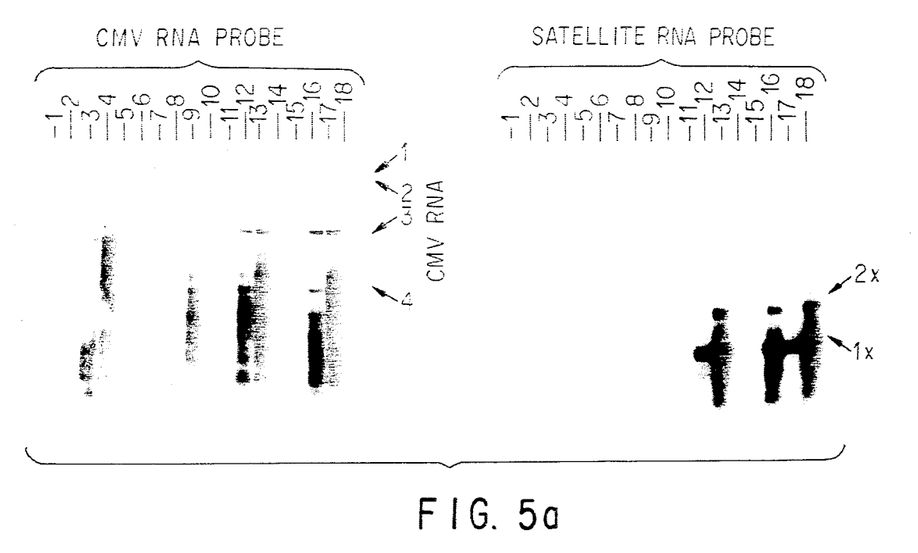
FIGS. 5a-5c shows the effect of CMV infection on the occurrence of satellite RNA in transformed plants.
Figure 5B:
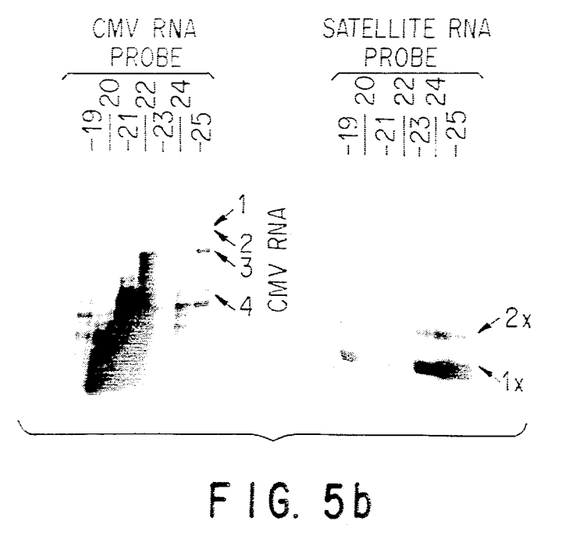
Figure 5C:
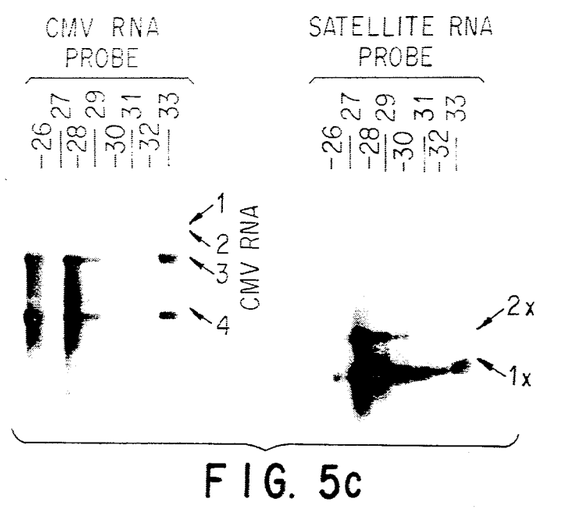

FIG. 5 shows the effect of CMV infection on the satellite RNA in transformed plants.

Leaves of transformed or non-transformed *N. tabacum* (var. Samsun NN) were inoculated with CMV strain R76B and 35 mm disks were cut 5 h later. Batches of 5 disks were floated on SPS medium (10 g l$^{-1}$ sucrose, 0.2 g l$^{-1}$ Ca (H$_2$PO$_4$)$_2$.H$_2$O, 0.3 g l$^{-1}$ sulphanilamide). Total RNA (1 µg) was isolated from these samples, or as indicated below, and analysed by Northern blotting as described for FIG. 4 using as probes the insert of pT105 (satellite RNA) or C20 (CMV RNA). The size markers were RNA of tissue infected with CMV alone (tracks 1 and 26) or CMV with satellite (tracks 18, 19 and 27) to show CMV RNA-1, CMV RNA-2, CMV RNA-3 and CMV RNA-4 or satellite monomer (1×) or dimer units (2×).

a) RNA in Primary Infections

Tracks 2-4 show RNA from disks of non-transformed plants, inoculated with CMV R76B and sampled at 5 h (track 2) post inoculation or 4 d (track 3) and 7 d (track 4) of incubation. Tracks 5 and 6 show RNA from disks of mock inoculated (non-transformed) plants at 4 d (track 5) or 7 d (track 6) incubation. Tracks 7-9 show RNA from a plant transformed with Rok1/C20. This is similar to Rok1/104 (FIG. 3) except that the insertion at the BamHI site of Rok1 was cDNA (C20) of the coat protein mRNA of CMV. The RNA was isolated at 5 h after infection (track 7) or from disks incubated for 4 d (track 8) and 7 d (track 9). Tracks 10-13 and 14-17 contain RNA from plants transformed with Rok1/104 or Rok1/105 respectively. The RNA was isolated before infection (tracks 10 and 14), 5 h after infection (tracks 11 and 15) and from disks at 4 d (tracks 12 and 16) and 7 d (tracks 13 and 17) of incubation.

b) RNA in Secondary Infections

Extracts of CMV-infected leaf disks, similar to those described in the experiment of FIG. 5a, were inoculated onto *Nicotiana clevelandii*. RNA was isolated from the systemically infected tissue after 10 days. The RNA (1 µg) was isolated from plants inoculated with extracts of disks of plants transformed with Rok1/C20 (tracks 20-22), Rok1/104 (track 23) or Rok1/105 (tracks 24, 25).

c) RNA in CMV Particles

Disks from CMV (R76B)-infected plants transformed with Rok1/105 were extracted at 7 d of incubation and the inoculum passaged through non-transformed *N. clevelandii* and re-inoculated onto *N. clevelandii*. After ten days of infection CMV particles were isolated from systemically infected leaves and the viral RNA extracted by addition of sodium dodecyl sulphate to 1% and treatment with phenol. Total cellular RNA was also isolated from this tissue for comparison. The samples shown are 100 ng virion RNA (track 33) or total cellular RNA (2.9 µg, track 28; 0.7 µg, track 29; 0.29 µg, track 30; 0.07 µg, track 31; 0.029 µg, track 32).

To determine the biological activity of these transcribed RNA molecules, the transformed plants were infected with CMV strain R76B. This is a satellite-free isolate of CMV obtained originally from a naturally infected raspberry plant in Scotland (ref 17). In one such test, disks were cut from leaves 5 h after inoculation. RNA was isolated from the disks, either at that time, or after floating the disks on SPS medium for 4 or 7 days. Northern blot analysis of the RNA with a probe for CMV (C20) (FIG. 5a) showed that by 4 days the CMV genomic RNAs had accumulated in disks both from the transformed and non-transformed plants. Many small RNA species which may represent subgenomic RNA species (ref 18) also accumulated over the same period (FIG. 5a). Satellite RNA was detected by Northern blot analysis after 4 days and 7 days but only in the disks from plants transformed with Rok1/104 or Rok1/105 (FIG. 5a). This RNA was present in large amounts and was primarily of unit satellite RNA length although, as is normal for an infection containing satellite, some dimers were also detected (FIG. 5a). At the loading of RNA and autoradiographic exposure of FIG. 5a, the transcribed satellite RNA molecules of about 700 and 1000 nucleotides were not detectable. The faint hybridisation of the satellite probe to high molecular weight RNA on some tracks of this gel is an artifact of aggregation of the probe with ribosomal RNA.

In further tests, sap from the disks sampled 4 and 7 days after inoculation was itself inoculated to *Nicotiana clevelandii*. Ten days after inoculation, RNA was isolated from the systemically infected leaves of these plants. Satellite RNA was detected by Northern blot analysis, in amounts typical of natural satellite RNA, and in unit and dimeric lengths, but only where the inoculum had been obtained from CMV-infected discs from plants transformed with Rok1/104 or Rok1/105 (FIG. 5b). The CMV probe detected viral genomic RNA in all samples (FIG. 5b).

In a similar experiment, a virus culture from CMV-infected plants which had been transformed with Rok1/105 was propagated twice in *N. clevelandii* and RNA was then isolated from CMV particles purified from these plants. Again unit and dimer length satellite RNA was detected in amount typical of a preparation containing natural satellite (FIG. 5c) although the amount of dimer was depleted in virions relative to the amount in total cellular RNA.

Unit and dimer length of satellite RNA were detected at high levels in extracts of systemically infected leaves, from CMV-inoculated plants which had been transformed with Rok1/104 and Rok1/195. Satellite RNA was not detected in extracts from systemically infected leaves of comparable non-transformed plants.

Clearly the transcribed satellite RNA in transformed plants can be processed to unit length molecules following CMV infection and subsequently acquired and perpetuated as a new part of the virus culture.

The ability to produce transcribed satellite RNA was inherited by the progeny of the plants transformed with Rok1/104 and Rok1/105. This was shown by Northern blot analysis of the poly A + RNA in the F1 progeny of these transformed plants, exactly as described above for the primary transformed plants (see reference to Northern blot analysis of FIG. 4).

F1 progeny of the transformed plants which had inherited the expression cassette with satellite cDNA and the associated DNA from the Rok1 vector were selected for this analysis by germination on MS medium (1 liter of MS medium contains 4.6 g Murashige and Skoog salt mixture (Flow Lab. cat no. 26-330-24), 0.1 g inositol, 0.01 g thiamine-HCl, 0.001 g nicotinic acid, 0.001 g pyridoxine HCl, 30 g sucrose. 7.0 g agarose at a final pH of 5.8) containing 1 micro g per ml kanamycin. The plants which carry the kanamycin resistance gene, originally derived from Rok1/105 or Rok1/104, are identifiable in this selection procedure as they show normal leaf greening and only slightly retarded leaf development. Tobacco plants which do not carry the kanamycin resistance gene fail to develop normal roots or green leaves. The kanamycin resistant seedlings were transferred from the kanamycin medium to soil or potting compost as soon as differential growth was observed between the kanamycin resistant seedlings and seedlings which had not inherited an active kanamycin resistance gene. The transcribed satellite produced in the F1 progeny plants was biologically active in the same way as the satellite RNA of the primary transformants. This was shown by infecting the F1 progeny plants with satellite RNA free virus (cucumovirus, see below) which caused the transcribed satellite RNA of the F1 progeny plants to be processed and replicated as unit length satellite RNA molecules which accumulated to a high level in the systemically infected leaves and which could be propagated as part of the virus culture during passage onto non-transformed plants. These effects were demonstrated using the methods described for the primary transformed plants (see reference above to FIG. 5b).

The transcribed satellite RNA was replicated as unit dimer length molecules, as described above, not only by CMV strain R76B, but also by other strains of cucumber mosaic virus. This was shown by infecting the transformed plants or their F1 progeny with CMV strain KIN or with CMV strain Y. CMV-KIN was isolated from a natural plant infection in Kinnaird, near Dundee and CMV-Y was obtained as RNA from Dr. Takanami of the Japan Tobacco and salt public Corporation, Umegaoka, Yokohama 227, Japan. A virus related to CMV, tomato aspermy virus (TAV) was also effective in causing the replication of transcribed satellite RNA. However, peanut stunt virus, which is distantly related to CMV, or brome mosaic virus, which is classed in a separate viral group from cucumber mosaic virus, were both not capable of causing the replication of transcribed satellite RNA.

The accumulation of satellite RNA in the transformed plants caused the properties of CMV infections to be modified on those plants. This was shown for CMV-R76B or CMV-KIN, inoculated onto either the primary transformed plants or onto the F1 progeny of those plants and by analysis of the viral RNA in the systemically infected leaves. In the plants producing transcribed satellite RNA the proportion of cellular RNA which has virus genomic RNA was less than 20% of the level in infected plants which were not producing transcribed satellite. The methods used to show this involved Northern blot analysis as described above.

Figure 6A:
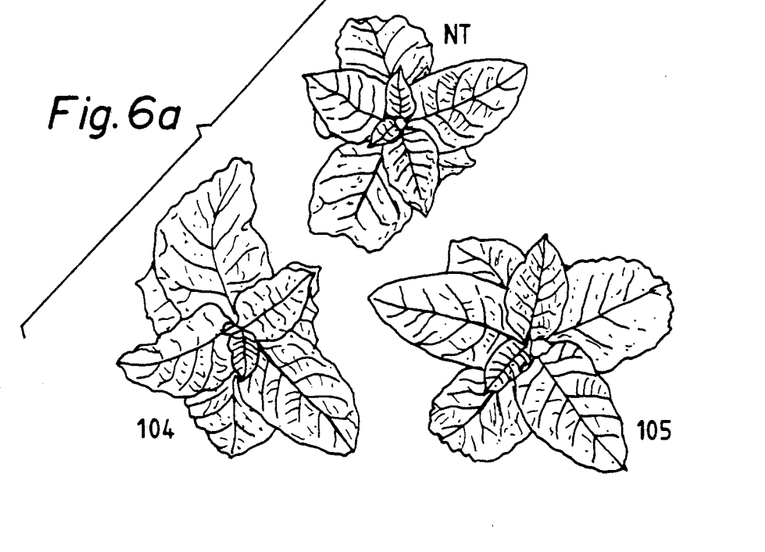
FIGS. 6a-6b shows the effect of transcribed satellite on symptom production.
Figure 6B:
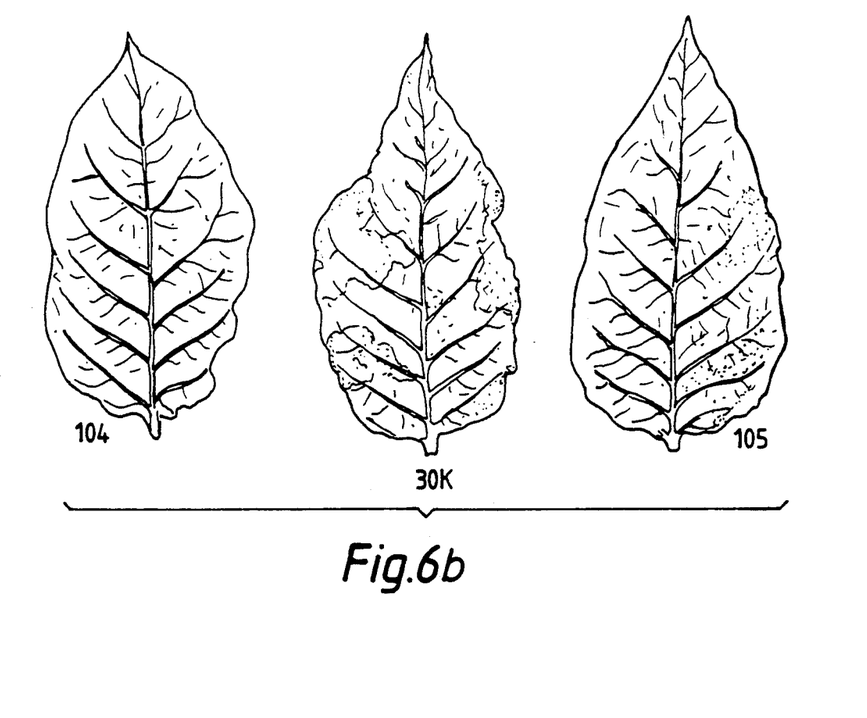

A second way in which the presence of transcribed satellite caused a modification of the CMV infection was shown in transformed plants which were inoculated with CMV-KIN and tomato aspermy virus. In these instances the symptoms of viral disease were much attenuated in the plants producing transcribed satellite RNA compared with non-transformed plants, or transformed plants which were not producing transcribed satellite RNA. This is illustrated in FIG. 6, which is an illustration of plants transformed with Rok1/104 and Rok1/105 and of non-transformed plants at approximately 4 weeks after infection with tomato aspermy virus. The effect was most obvious in the systemically infected leaves in which the mosaic and leaf distortions produced by the tomato aspermy virus were absent from the plants producing transcribed satellite RNA. Transformed plants or non-transformed plants were inoculated with tomato aspermy virus and photographed 4 weeks after infection. a) shows the intact plants and b) systemically infected leaves. 104 and 105 are the transformed plants expressing satellite, as described above. 30K is a transformed plant, expressing a sequence of tobacco rattle virus and is a control to show that transformation per se has no effect on symptom production. NT is a non-transformed plant.

This symptom attenuation effect with TAV was independent of the strength of the inoculum and the length of the infection up to six weeks post-inoculation, which is the latest time tested. The effect was highly reproducible, being observed in all of the plants producing transcribed satellite which were tested.

CMV or TAV cultures which acquired satellite RNA as a result of passage through plants which were producing transcribed satellite RNA also showed modified properties. This was demonstrated when *Nicotiana clevelandii* plants were inoculated with CMV or TAB which had been passaged through various tobacco plants as described above with reference to FIG. 5b. The disease symptoms were reduced markedly when the inoculum had been passaged through plants which were producing transcribed satellite RNA.

REFERENCES

1. Lot, H. et al. Annals Phytopath. 4, 25–38 (1972).
2. Viera, J. and Messing, J. Gene 19, 259–268 (1982).
3. Maxam and Gilbert, W. Methods Enzymol. 65, 499–560 (1977)
4. Melton, D. A. et al. Nucleic Acids Res. 12, 7035–7056 (1984).
5. Messing, J. Methods Enzymol. 101, 20–79 (1983).
6. Sanger et al. J. Mol. Biol. 143, 161 et seq (1980).
7. Tabor, S. and Richardson, C. C. Proc. Natl. Acad. Sci. USA 82, 1074–1078 (1985).
8. Bevan, M. Nucleic Acids Res. 12, 8711–8721 (1984).
9. Bevan, M. et al. EMBO K. 4, 1921–1926 (1985).
10. Guilley, H. et al. Cell 30, 763–773 (1982).
11. Bevan, M. et al. Nucleic Acids Res. 11, 369–385 (1983).
12. Horsch, R. B. et al. Science 227, 1229–1231 (1985).
13. Gould, A. R. and Symons, R. H. Eur. J. Biochem. 126, 217–226 (1982).
14. Apel, K. and Kloppstech, K. Eur J. Biochem. 85, 581–588 (1978).
15. Goldberg, D. A. Proc. Natl. Acad. Sci. USA. 77, 5794–5798 (1980).
16. Thomas, P. S. Proc. Natl. Acad. Sci. USA, 77, 5201–5202 (1980).
17. Jones, A. T. Rep. Scott. Crop. Res. Inst. 1983, 197–198 (1984).
18. Gordon, K. H. J. and Symons, R. H. Virology 142, 144–157 (1985).
19. Richards et al. Virology 89, 395–408 (1976).
20. Jacquemond, M. & Lot. H., Agronomie 1, 927–932 (1981).

We claim:

1. A method of protecting a plant against the effects of a plant virus, said method comprising:
    transferring a DNA fragment into a plant, wherein the DNA fragment is complementary to a symptom-attenuating satellite RNA sequence of a first Cucumovirus,
    said DNA fragment being capable of being transcribed in said plant and inherited by a progeny plant; and when transcribed, or when transcribed and translated in said plant or progeny plant, said DNA fragment protects said plant by attenuating the symptoms brought about by infecting said plant with a second Cucumovirus.

2. The method of claim 1, wherein the DNA fragment is transferred into the plant by a recombinant vector carrying the fragment.

3. The method of claim 1, wherein the DNA fragment is transferred into the plant by allowing the direct uptake of the fragment by the plant cells.

4. The method of claim 1, wherein the first and the second Cucumoviruses are the same virus.

5. The method of claim 4, wherein the Cucumovirus is cucumber mosaic virus (CMV).

6. The method of claim 1, wherein the satellite RNA or the corresponding DNA fragment is modified prior to transfer onto the plant.

7. The method of claim 1, wherein the DNA fragment is a cDNA fragment derived from the satellite RNA.

8. The method of claim 1, wherein the satellite RNA comprises a multimeric RNA structure.

9. The method of claim 1, wherein the DNA fragment is transferred into the genome of a plant.

10. The method of claim 2 wherein said recombinant vector, carrying said DNA fragment into said plant, contains a plasmid comprising:

T-DNA border sequences of the Ti plasmid of Agrobacterium tumefaciens;

a transcriptional promotor;

a DNA fragment complementary to satellite RNA of a Cucumovirus; and a transcriptional terminator.

11. The method of claim 10, wherein the transferring step is conducted by infecting cells of the plant with a strain of *A. tumefaciens* comprising the recombinant vector;

allowing the DNA fragment to be transferred into the cells; and regenerating whole plants from the infected, transformed cells.

12. The method of claim 10, wherein the DNA fragment is transferred into the genome of the plant.

13. A method of modifying the effects of a plant virus, said method comprising;

transferring a DNA fragment into a plant, wherein the DNA fragment is complementary to a symptom-attenuating satellite RNA sequence of a first Cucumovirus, said DNA fragment being capable of being transcribed in said plant and inherited by a progeny plant; and when transcribed, or when transcribed and translated in said plant or a progeny plant, said DNA fragment modifies the effects of said virus by attenuating the symptoms brought about by infecting said plant with a second Cucumovirus.

14. A plant produced by the method of claim 1, wherein said plant contains said transferred DNA fragment and said plant has the ability to produce transcribed satellite RNA, and wherein said plant is capable of transmitting said DNA fragment to a progeny plant; or a progeny plant from said plant produced by the method of claim 1, wherein said progeny plant inherits said DNA fragment and has the ability to produce transcribed satellite RNA.

* * * * *